United States Patent [19]

Bobo, Jr. et al.

[11] Patent Number: 4,846,792
[45] Date of Patent: Jul. 11, 1989

[54] AUTOMATIC INFILTRATION DETECTION SYSTEM AND METHOD

[75] Inventors: Donald E. Bobo, Jr., Irvine; Dennis R. Seguine; Theodore R. Lapp, both of Mission Viejo, all of Calif.

[73] Assignee: Baxter International Inc., Deerfield, Ill.

[21] Appl. No.: 165,619

[22] Filed: Mar. 8, 1988

[51] Int. Cl.[4] .............................................. A61M 5/00
[52] U.S. Cl. ...................................... 604/50; 604/67; 128/DIG. 13
[58] Field of Search ................ 604/50, 65–67, 604/118, 245, 246; 128/DIG. 12, DIG. 13, 748

[56] References Cited

U.S. PATENT DOCUMENTS

| | | | |
|---|---|---|---|
| 3,690,318 | 9/1972 | Gorsuch et al. | 604/141 |
| 4,140,110 | 2/1979 | Jansen et al. | |
| 4,392,847 | 7/1983 | Whitney | 604/118 |
| 4,468,219 | 8/1984 | Georges et al. | 604/66 |
| 4,648,869 | 3/1987 | Bobo, Jr. | |
| 4,657,529 | 4/1987 | Prince et al. | |
| 4,710,163 | 12/1987 | Butterfield | |

Primary Examiner—Stephen C. Pellegrino
Attorney, Agent, or Firm—Debra E. Dahl; Gordon L. Peterson

[57] ABSTRACT

An infusion system for infusing a fluid into a patient comprising an infusion device for delivering the fluid in both a normal delivery pattern and a test pulse and a conduit for conducting the fluid from the infusion device to the patient. The test pulse creates a pressure wave response in the conduit. Abnormal infusion can be detected by determining the area between a baseline and at least a portion of a pressure versus time curve representing the pressure wave response.

45 Claims, 5 Drawing Sheets

AUTOMATIC INFILTRATION DETECTION SYSTEM AND METHOD

BACKGROUND OF THE INVENTION

It is often necessary or desirable to infuse a flowable material or fluid, which may be liquid, a gas or a combination thereof, into a patient. One example is the administration of parenteral fluids to a patient.

A typical infusion system includes an infusion device for delivering the fluid and conduit means for conducting the flowing material from the infusion device to the patient. The conduit means typically comprises flexible tubing leading from the infusion device and a cannula, such as a needle or catheter, for insertion into the vascular system of the patient. In normal operation, the infusion device delivers the fluid through the tubing and the needle to the vascular system of the patient.

One problem with infusion systems of this type is a condition known as infiltration. Infiltration is a condition in which infused fluid finds its way into extravascular tissues rather than simply being released into the blood stream. Such a situation occurs when the needle is not in communication with the interior of the vessel into which the fluid is to be infused. When this occurs, fluid is infused into the interstitial spaces between layers of tissues. Thus, the patient is deprived of proper intravenous drug administration and is further subjected to possible toxic or caustic effects associated with infused fluids being in direct contact with body tissues. Infiltration is not the only possible type of anomaly associated with intravenous therapy which can cause the fluid to be improperly supplied to the patient. Other conditions which can cause abnormal infusion, i.e., the fluid to be improperly supplied to the patient, include venous inflamation and swelling at the infusion site (phlebitis), clotting and a wide variety of obstructions of the conduit means, such as kinking of the tubing which supplies the fluid to the patient. Many of these affect fluid flow characteristics in a manner similar to infiltration and can, therefore, be detected by infiltration detection devices.

The goal of an infiltration detection system is to identify an abnormal infusion as early as possible without generating an excessive number of false alarms. Early detection allows the attending medical staff to rectify the problem before significant damage has been done by the infiltration and before the patient has been deprived of a significant amount of the intravenous therapy. On the other hand, if the detection system is too sensitive, false alarms will result. This is very undesirable since, from a clinical perspective, establishing a new intravenous site can be difficult and time consuming. During the time necessary to start the new IV, which can be hours in some cases, the patient is not receiving the desired treatment.

Bobo U.S. Pat. No. 4,648,869 discloses a significant advance in the field of infiltration detection systems and methods. According to the Bobo patent, an infusion system infuses a test pulse of fluid to a patient. The test pulse creates a pressure wave response which can be monitored and used to detect if abnormal infusion has occurred.

Butterfield U.S. Pat. No. 4,710,163 discloses an infiltration detection system which uses the test pulse-pressure wave response concept of the Bobo patent. However, the Butterfield system compares the pressure wave response with a reference pressure wave response which represents the normal response when there is no infiltration. Specifically, the area between two curves representing these responses is used to attempt to detect infiltration. Thus, the Butterfield approach has the disadvantage of requiring that a normal pressure wave response be first determined and then stored for later comparison.

SUMMARY OF THE INVENTION

This invention provides a novel and improved technique for detecting abnormal infusion, i.e., if fluid is being improperly supplied to a patient. To make this determination, this invention utilizes the area between a baseline and at least a portion of a pressure versus time curve which represents the pressure wave response. With this technique, it is not necessary to first establish a normal pressure wave response for a patient, nor is it necessary to compare this assumed normal response to the pressure wave response. Rather, with this invention, all that is required to make accurate determinations as to the proper supply of fluid to a patient is appropriate area information from the pressure wave response.

This invention provides an apparatus for determining if fluid is being properly supplied through a fluid delivery system to a patient, and such apparatus includes means for delivering fluid through the delivery system so as to create a pressure wave response in the delivery system. This may be accomplished, for example, in accordance with the teachings of Bobo U.S. Pat. No. 4,648,869, which is incorporated by reference herein. Thus, as disclosed in the Bobo patent, the fluid may be delivered in both a normal delivery pattern and a test pulse, with the test pulse creating a pressure wave response in the delivery system.

The apparatus also includes means for determining the area between a baseline and at least a portion of a pressure versus time curve which represents the pressure wave response, and means responsive to the magnitude of such area for detercting if the fluid is being improperly supplied by the fluid delivery system to the patient.

The pressure wave response has a peak value of pressure and a leading portion and a trailing portion on opposite sides of the peak value. When fluid is being properly supplied to the patient, the pressure will rise rapidly but typically not to a very high peak value. However, if the fluid is being improperly supplied to the patient as when infiltration occurs, the pressure will rise to a higher peak value over a longer period of time. The peak pressure is large because the infused fluid has no immediate means of escape from the interstitial spaces. After termination of the test pulse, the pressure will drop rapidly to its nominal level if the fluid is being properly supplied to the patient. In the case of abnormal infusion, the pressure drops much more slowly from the peak value because there is no immediate escape path for the fluid.

The integration technique of this invention uses an area characteristic of the pressure wave response to determine if fluid is being improperly supplied to the patient. The function integrated is the difference between a baseline and a curve representing the pressure wave response and extends along the curve from an initial point to a truncation point. Although the baseline can be established in different ways, preferably, the baseline is established as a function of the pressure in the delivery system when the test pulse and, hence the pressure wave response, are not present. The baseline used for the integration is preferably held essentially constant during the integration.

The truncation point, or upper limit on the integration, preferably is on the trailing portion of the curve corresponding to the trailing portion of the pressure wave response, i.e., it preferably occurs after the peak value of pressure has been attained. Although it is possible to truncate the integration prior to or at the peak value of pressure, because the peak pressure is typically drastically different when the fluid is being improperly supplied to the patient, it is highly desirable to include, and go beyond, the peak value for the integration.

The output from an infusion pump used to deliver the fluid to the patient may not be totally uniform, and preferably, the truncation point occurs at a time which is sufficiently beyond the peak value of pressure so as to take this into account. Typically, it is preferred that the truncation point be at a time at which the pressure is no greater than about 70 percent of the peak value.

On the other hand, the truncation point is preferably essentially outside of the noise range, and this typically means that it occurs at a time at which the pressure is no less than about 30 percent of the peak value. Thus, the truncation point is preferably at a time at which the pressure is between about 30 and about 70 percent of the peak value with about 50 percent being considered optimum. The initial point, or lower limit on the integration, is preferably essentially at the beginning of the point of the curve corresponding to the beginning of the pressure wave response.

Alternatively, or in addition thereto, the integration of the pressure wave response may extend from the initial point to about the peak value of pressure. Such an integration would determine a front end area. The detecting means may be responsive to either or both of the front end area and the truncated area, i.e., the area established by integrating the pressure wave response from the initial point to the truncation point. Preferably, the detecting means is responsive to both of these areas.

The infusion device should be capable of delivering the fluid in a test pulse. Broadly, it is only necessary that the test pulse be capable of creating a pressure wave response in the delivery system. Typically, to accomplish this, the test pulse must be distinguishable from the normal delivery pattern.

The test pulse can be distinguished from the normal delivery pattern in different ways. For example, the test pulse can be separated from the normal delivery pattern by separating regions on one or both sides of the test pulse, with each of the separating regions providing a different flow rate of fluid than the adjacent portions of the test pulse. In a broad sense, the separating regions may have flow rates equal to the flow rate of the normal delivery pattern. Preferably, however, the infusion device is capable of delivering the fluid in an altered pattern which includes a test pulse and leading and trailing valleys on opposite sides of the test pulse. The test pulse provides a greater flow rate of fluid than the normal delivery pattern, and each of the valleys provides a lesser flow rate of fluid than the adjacent portions of the normal delivery pattern. When this form of infusion is used, the truncation point is preferably established as the first to occur of a specified percent of peak value and the termination of the trailing valley. This is desirable because, in the case of infiltration, where the pressure wave response decays slowly, the predetermined percent of peak value may not be reached. With this form of infusion, the initial point may coincide with the beginning of the test pulse.

The flow rate during the test pulse may be less than, greater than, or equal to the flow rate during the normal delivery pattern. However, the preferred altered pattern, as described above, has several advantages, including the advantage of preventing the test pulse from significantly altering the average flow of fluid to the patient. It is also possible to reverse the flow in the delivery system to create the test pulse. However, this is not preferred because it may cause the patient's vessel to collapse around the needle.

The area information from the test pulse can be processed in various different ways to determine if the fluid is being properly or improperly supplied to the patient. Generally, a larger area indicates an alarm condition, and a smaller area is indicative of normal infusion. The areas are also a function of test pulse infusion rates. Of course, information from multiple pressure wave responses derived from multiple test pulses can be processed to gain greater assurance that the infusion system is being correctly monitored.

Another important feature of this invention is ascertaining if the pressure conditions in the conduit are suitable for detecting abnormal infusion. It has been found that the occurrence of a baseline pressure during the normal delivery pattern which is unusually large in magnitude or which fluctuates excessively, suggests that the pressure conditions in the conduit are not then suitable for detecting abnormal infusion. Such baseline conditions may be the result of a transient condition, such as movement by the patient. When these pressure artifacts occur, either the application of the test pulse is deferred or the data derived from such test pulse is ignored.

The presence of these unacceptable pressure disturbances in the baseline indicate that the pressure conditions are not suitable for detecting abnormal infusion, and one reason for this is that these pressure artifacts would be superimposed upon the pressure wave response. This would tend to unacceptably alter the pressure wave response such that the pressure wave response would not be indicative of the health of the IV site, but rather indicative of some other condition, such as unusual patient movement. This feature of the invention is applicable to virtually any abnormal infusion detection system, which is responsive to the pressure wave response, and is not limited to use with a system which detects abnormal infusion by integration techniques.

More specifically, the suitability of the pressure conditions in the conduit can be determined by comparing a function of the pressure of the fluid in the conduit during the normal delivery pattern to a threshold. This function of the pressure may be one or more pressure values or may be a function which is derived from one or more pressure values. In a preferred technique, the function of the pressure equals $B1 + K(B2)$ where $B1$ is the baseline pressure at an instant prior to the test pulse, $K$ is a constant, and $B2$ is the rms value of a plurality of segments of the baseline pressure prior to the test pulse, and with at least one of the segments being prior to such instant.

The invention, together with additional features and advantages thereof, may best be understood by reference to the following description taken in connection with the accompanying illustrative drawing.

DESCRIPTION OF THE PREFERRED EMBODIMENT

Figure 1:
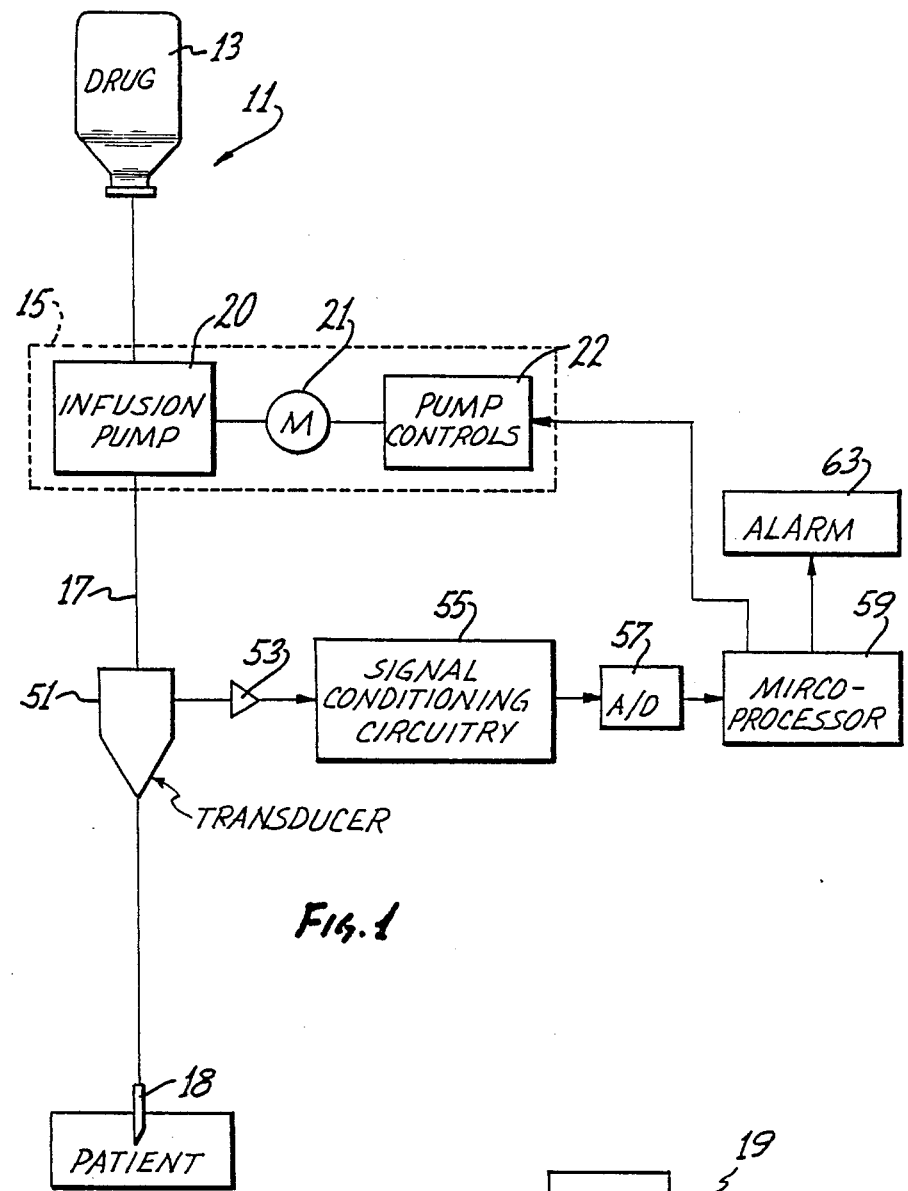
FIG. 1 is a block diagram illustrating one form of infusion system constructed in accordance with the teachings of this invention.

FIG. 1 shows an infusion system 11 which comprises a source 13 of a parenteral fluid, an infusion device 15 for delivering the parenteral fluid through conduit means 17 to a patient. The conduit means 17 may comprise flexible tubing or other flow channels for supplying the parenteral fluid to the patient. The conduit means terminates in a needle 18, such as an I.V. needle, which is adapted to be inserted into a vessel of the patient's vascular system so that the open distal end of the needle communicates with the interior of the vessel. In this embodiment, the needle 18 is inserted into a vein. If the open distal end of the needle communicates with tissue, as wehn the needle is forced completely through the vessel wall, infiltration has occurred.

The infusion device 15 may be any infusion device which is controllable to produce a test pulse 19 (FIG. 2) and, as such, may include an infusion pump, a controller, syringe or the like. In this embodiment, the infusion device 15 includes a motor, such as a stepping motor 21, for driving the pump and pump controls 22 for controlling the motor. The pump 20 is a positive displacement pump, and accordingly, its output can be controlled by controlling the speed of the motor 21. The pump controls 22 control the motor speed as described more fully hereinbelow to provide the infusion device with the desired output.

In a preferred construction, the infusion device 15 is a peristaltic pump of the type disclosed in U.S. application Ser. No. 661,032 entitled Continuous Delivery Peristaltic Pump and filed on Oct. 15, 1984. Such an infusion pump has a normal delivery pattern 25 which, in this example, is essentially constant as shown by the flat portions of the pump delivery curve of FIG. 2. This is the result of accelerating through the deadband of the peristaltic pump. The curve of FIG. 2 is somewhat idealized in that the preferred infusion pump provides periodic short spikes and valleys of exceedingly short duration; however, these are sufficiently insignificant so that the normal delivery pattern of the pump can be considered as essentially constant, although a constant flow rate during the normal delivery pattern is not required.

Figure 2:
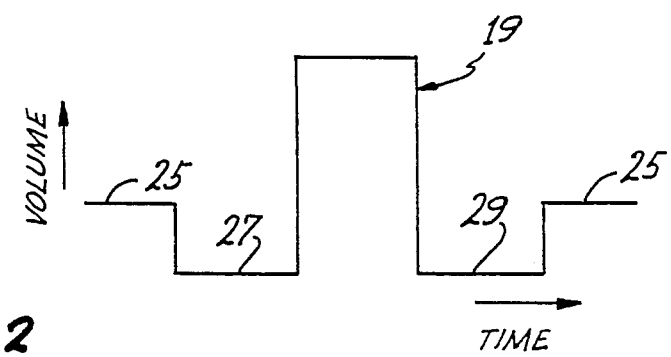
FIGS. 2-2E are plots of volume delivered by the infusion device versus time illustrating different examples of test pulses.

The pump controls 22 periodically, and/or on demand, increase the speed of the stepping motor 21 to cause the infusion pump 20 to provide the test pulse 19 which, in the illustrated embodiment of FIG. 2, is in the form of an essentially square wave having a duration of approximately four seconds. As described more fully in Bobo U.S. Pat. No. 4,648,869 the infusion rate, and hence the volume delivered, during the test pulse preferably varies with the selected infusion rate for the infusion device 15. However, the duration of the test pulse 19 may be constant for all selected infusion rates. Selection of the infusion rate also results in selection of the associated flow rate for the test pulse 19. In this regard, the pump controls 22, as is common for infusion devices of this type, are programmable to enable the attendant to select or punch in a desired or selected infusion rate.

The pump controls 22 reduce the speed of the stepping motor 21 just before and just after each test pulse 19 to cause the infusion pump 20 to provide separating regions, which in this embodiment, are leading and trailing infusion valleys 27 and 29, respectively, contiguous to, and on opposite sides of, the test pulse 19. The valleys 27 and 29 are square waves of short duration during which the infusion rate is reduced sufficiently to wholly or partially compensate for the increased infusion rate which takes place during the test pulse 19. Preferably, the valleys 27 and 29 reduce the total flow by the same amount that the test pulse increases it so that the average or net effect across the valleys 27 and 29 and the test pulse 19 is an infusion rate equal to the rate represented by the normal delivery pattern 25. For example, each of the valleys 27 and 29 may have a duration which is twice as long as the duration of the test pulse 19, with such duration being 8 seconds in this embodiment and constant for all selected infusion rates. The test pulse 19 and the valleys 27 and 29 constitute an altered pattern of flow.

Test pulses can be provided in various different ways, and additional examples of test pulses, which can be distinguished from the normal delivery pattern, are shown in FIGS. 2A-2E. Portions of the curves shown in FIGS. 2A-2E corresponding to portions of the curve shown in FIG. 2 are designated by corresponding reference numerals followed by the letter "a", "b", "c", "d", and "e", respectively.

Figure 2A:
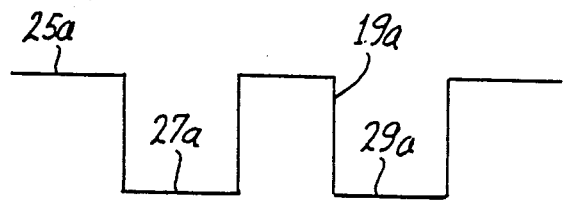

In FIG. 2A, the test pulse 19a is separated from the normal delivery pattern 25a by leading and trailing valleys 27a and 29a in much the same manner as disclosed in FIG. 2. However, the infusion rate during the test pulse 19a is the same as the infusion rate during the normal delivery pattern 25a. Although the infusion rates during the valleys 27a and 29a can be "0" or negative, preferably, the infusion rates during these times are positive. Also, although the infusion rates during the valleys 27a and 29a can be different, preferably, they are essentially the same.

Figure 2B:
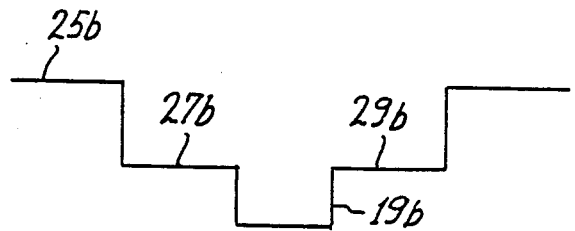

In FIG. 2B, the test pulse 19b is negative, i.e., the infusion pump 20 is reversed to create the infusion pulse. Although the infusion rate during the valleys 27b and 29b may be either positive or negative, in this embodiment, they are essentially "0."

Figure 2C:
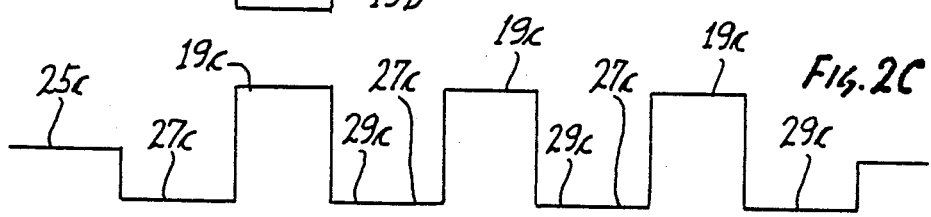

In FIG. 2C, a plurality of test pulses 19c is provided in relatively rapid succession before the infusion rate returns to the normal delivery pattern 25c. In this event, the valleys 27c and 29c between adjacent test pulses 19c constitute both trailing and leading valleys as shown.

Figure 2D:
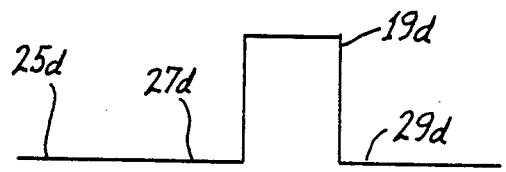

In FIG. 2D, the separating regions 27d and 29d are not distinguishable from the normal delivery pattern 25d, and so the altered pattern of delivery consists only of the test pulse 19d. This can be contrasted with the embodiments described above in which the altered pattern comprises both the leading and trailing separating regions and the test pulses.

Figure 2E:
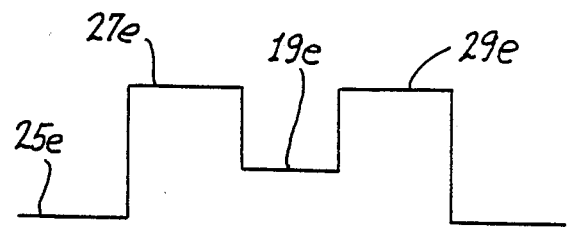

In FIG. 2E, the separating regions 27c and 29e represent periods during which the flow rate is greater than during the normal delivery pattern 25e, and the test pulse 19e represents a decreased flow rate which may be equal to, greater than or less than the flow rate during the normal delivery pattern. As illustrated, the flow rate during the test pulse 19e is greater than the flow rate during the normal delivery pattern 25e. Generally, test pulses of the type shown in FIGS. 2B and 2E, which have flow rates less than the adjacent separating regions, are not preferred.

Figure 3:
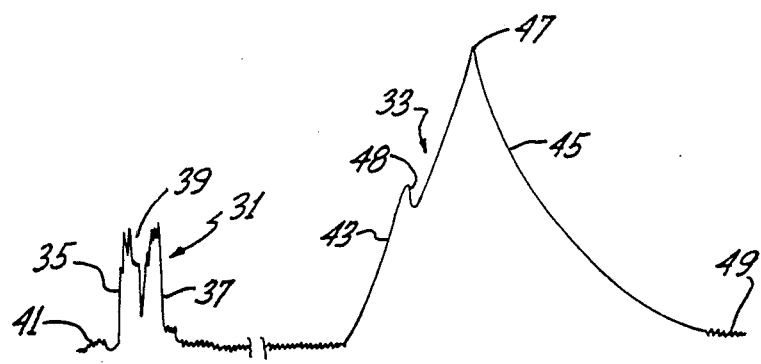
FIG. 3 is a plot showing one pressure wave response indicative of the fluid being properly supplied to the vessel of a patient and a second pressure wave response indicative of infiltration.

The presence of the test pulse 19 in the conduit means 17 creates a pressure wave response which has different characteristics depending upon whether or not the flowable material is being improperly supplied by the conduit means 17 to the patient. FIG. 3 shows examples of pressure wave responses 31 and 33 which indicate in-the-vessel and infiltration conditions, respectively. Although the pressure wave responses 31 and 33 are both shown in FIG. 3, they are not in scale in relation to each other. In reality, FIG. 3 shows curves which represent the pressure wave responses, but the curves, if desired, can be considered as the pressure wave responses.

The pressure provided by the pressure wave response 31 rises rapidly and almost instantaneously along a rising edge 35 and decays at about the same rate as represented by a falling edge 37. In between the edges 35 and 37, the pressure remains approximately constant, except for a short duration valley 39 which is representative of the deadband of the peristaltic pump being employed. In this regard, the pressure wave response 31 was generated by a peristaltic pump having a deadband and operating at about 350 cc's per hour, which is a high-delivery rate. If a peristaltic pump which accelerates through the deadband were employed, the duration and magnitude of the valley 39 would be greatly reduced. For this reason, it is preferred to utilize a peristaltic pump which does accelerate through the deadband so that any valley 39 would be of substantially less magnitude and duration than illustrated in FIG. 3. However, the pressure wave response 31 is essentially a square wave if the valley 39 is ignored. With the open distal end of the needle 18 of the conduit means 17 properly communicating with the interior of the vessel of the patient's cardiovascular system, the pressure wave response 31 is simply the result of forcing the additional fluid into the fluid carried by the vessel. For example, for an infusion rate of 5 cc/hour, the pressure wave response 31 may rise about 5 mm Hg above a base line.

When infiltration occurs, the open distal end of the needle 18 is out of the interior of the vessel and communicates with tissue. As a result, the pressure wave response 33 is created in the conduit means 17. Specifically, the pressure wave response 33 rises along a rising edge or leading portion 43 and falls along a falling edge or trailing portion 45 with both the rise time and fall time being much greater than for the pressure wave response 31. In addition, the pressure wave response 33 has a maximum pressure or peak value 47 which is much higher than the maximum pressure or peak value of the pressure wave response 31. For example, for an infusion rate of 5 cc/hour, the pressure wave response 33 may rise about 20 mm Hg above a baseline 49. The rising edge has a discontinuity 48 which is the result of using a peristaltic infusion pump to generate the pressure wave response 33 which did not accelerate through the deadband and, therefore, did not have an essentially constant delivery rate.

The pressure, or pressure response, of the parenteral fluid in the conduit means 17 can be monitored in various different ways, such as by a pressure transducer 51 which provides an electronic analog pressure signal which is related to the pressure in the conduit means 17. In this embodiment, the pressure signal from the transducer 51 is amplified by an amplifier 53, conditioned in signal conditioning circuitry 55 and sampled in an analog-to-digital converter (A/D converter) 57 which provides the samples to a microprocessor 59. The signal conditioning circuitry 55 is conventional and is provided for the purpose of adjusting or compensating for various variables, such as temperature. Of course, if these variables are not considered significant, the signal conditioning circuitry 55 can be eliminated.

The samples of the pressure signal from the transducer 51 may be taken continuously or taken only during the sample time. In the former case, the microprocessor 59 is used to separate the samples taken during the sample time from those which are not. However, in this embodiment, the A/D converter 57 samples the pressure signal continuously and provides the samples in a digital format to the microprocessor 59.

The sampling frequency of the A/D converter 57 is preferably higher than the sampling frequency required for detecting infiltration or other abnormal infusion. For example, if infiltration detection requires about one sample per second, samples may be taken at, for example, 5 samples per second, 40 samples per second, etc. The samples can then be combined in any of a variety of ways to produce an overall sample value for each second by the microprocessor 59. In any event, the microprocessor 59 performs an integration function as described below to determine if infiltration has occurred.

Figure 4:
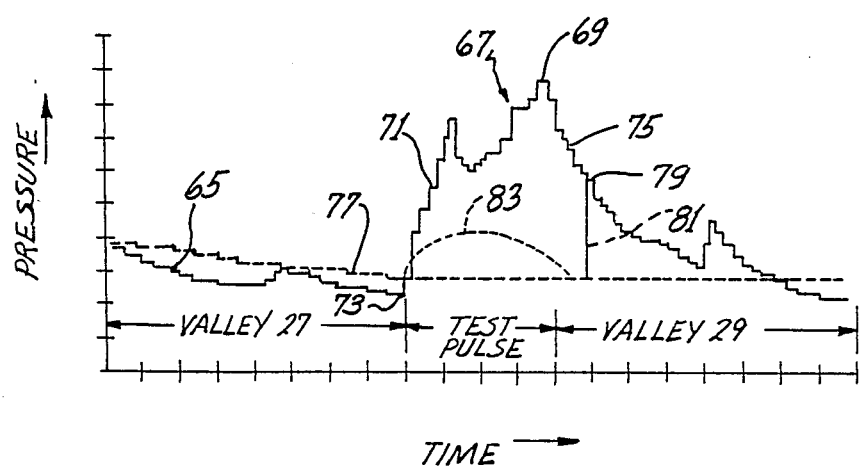
FIG. 4 is a plot showing the relationship of the pressure response to the infusion rate for infiltration conditions and normal conditions.

FIG. 4 shows a pressure response 65 in the conduit 17 as measured by the transducer 51 in response to infusion of fluid through the conduit to the patient. As shown, the pressure generally diminishes during the valley 27 until the leading edge of test pulse 19, at which time a pressure wave response 67 is initiated. The response 67 is indicative of abnormal infusion, e.g., infiltration. The pressure wave response 67 rises, with modest interruption to a peak value 69 of pressure which is reached at approximately the end of the test pulse 19. The pressure then slowly decays during the valley 29, again with modest interruption, to the end of the valley 29. Thus, the pressure wave response 67 has a leading portion 71 that extends from an initial point 73 at the beginning of the test pulse 19 to the peak value 69 and a trailing portion 75 that extends from the peak value 69 to a baseline 77.

The baseline 77 can be established by the microprocessor 59 in various different ways and is preferably a function of the pressure response 65 intermediate test pulses 19. More specifically, the baseline 77 can be established by suitably smoothing the pressure response 65 between test pulses 19, and this function can be carried out by the microprocessor. Accordingly, the baseline 77 lags the pressure response 65. However, at the initiation of the test pulse 19, the baseline 77 then existing is frozen by the microprocessor such that it remains essentially constant throughout at least the test pulse 19 and the trailing valley 29.

Various different techniques can be used to smooth the pressure response 65 between test pulses 19. According to one preferred smoothing technique, the pressure samples from the A/D converter 57 are slew-rate limited and averaged to provide pressure values for updating the baseline 77. By way of illustration and not by way of limitation, the A/D converter 57 may provide 40 pressure samples per second, and the slew-rate limiting processing limits each sample to a value which is no greater than 1.25 times, and no less than 0.75 times the value of the previous sample. Following this, a ¼ second average of ten of the samples is taken, and this average value provides a new point for updating the baseline 77. With this technique, four new smoothed pressure readings are provided each second. The baseline 77 is then typically derived by passing these samples through an additional smoothing process, such as a single-pole low-pass filter with a time constant of about 2 seconds.

A primary advantage of slew-rate limiting is to eliminate spurious spikes that may occur in the pressure response 65 that might be incorrectly interpreted as the peak value 69. In addition, slew-rate limiting and averaging provides a desired smoothing effect for the baseline 77 to reduce transient irregularities that might otherwise occur in the baseline 77.

To determine if infiltration or other abnormal infusion has occurred, the area between the pressure wave response 67 and the baseline 77 is calculated by the microprocessor between the initial point 73 and a truncation point 79. In this embodiment, the truncation point 79 is the time at which the pressure on the trailing portion 75 drops to 50 percent of the peak value 69. More generally, the truncation point 79 is the first to occur of a pre-established percent of the peak value 69 and the end of the trailing valley 29. Because in the example of FIG. 4, the predetermined percent of the peak value 69 occurred first, the integration is truncated at this point along a line 81.

Alternatively, or in addition thereto, the integration of the pressure wave response 67 may proceed from the initial point 73 to the peak value 69 to provide a front end area. This front end area may be used in lieu of, or in addition to, the truncated area, i.e., the area obtained from integrating from the initial point 73 to the truncation point 79, to determine whether or not infiltration has occurred.

FIG. 4 also shows a somewhat idealized pressure wave response 83 in dashed lines which is indicative of the proper supply of fluid to the patient. The pressure wave response 67 and 83 would, of course, not exist simultaneously, but they are shown together for comparative purposes. Applying the same criteria for integration of the pressure wave response 83, virtually the entire area between the pressure wave response 83 and the baseline 77 would be determined. However, this area is much less than the area obtained by the truncated integration of the pressure wave response 67. Accordingly, the microprocessor 59 can readily determine whether or not infiltration has occurred.

The area information can be used in various different ways to arrive at a decision regarding the presence or absence of infiltration or other abnormal infusion. For example, both the truncated area and the front end area may be normalized and compared with known thresholds, and an alarm condition may be declared in response to one or more of these areas exceeding the established threshold. In a preferred decision-making technique, an alarm condition is not declared until three consecutive normalized truncated areas or three consecutive normalized front end areas resulting from three consecutive test pulses have exceeded their respective thresholds. More specifically, in one technique, the truncated area is normalized by dividing it by a divisor which is a function of the difference between the infusion rate during the test pulse and the infusion rate during either of the valleys 27 and 29. Preferably, the function is simply the difference between these infusion rates. The quotient or normalized area is then compared with a known threshold. The front end area is normalized in the same way and compared with its threshold.

It has been found that the threshold varies with a number of factors, the most important of which is the gauge or size of the needle 18. The areas can be effectively normalized for needle (or other cannula) size by employing different thresholds for different ranges of needle size. Examples of suitable thresholds for both truncated area and front end area as a function of needle gauge are shown in the table below:

| Needle Gauge | Thresholds | |
| --- | --- | --- |
| | Front-End Area | Truncated Area |
| 16–18 | 0.1 | 0.2 |
| 19–21 | 0.3 | 0.6 |
| 22 and above | 0.5 | 1.0 |

Thus, if a 16-gauge needle is used, an alarm condition indicative of abnormal infusion would be declared if any three-consecutive test pulses yielded a normalized truncated area of greater than 0.2 or a normalized front end area of greater than 0.1.

In the above table, it is assumed that the units on the area of pressure wave response are mmHg-seconds and that the infusion rates are in milliliters per hour. Of course, different units can be employed, and the thresholds adjusted accordingly.

Another feature of this invention is to ascertain if pressure conditions in the conduit means 17 are suitable for detecting if fluid is being improperly supplied by the conduit means to the patient. Although this feature of the invention is particularly adapted for use with the integration technique of this invention, its use is not so limited, and it can be used with other techniques for determining whether or not abnormal infusion exists.

The suitability of the pressure conditions in the conduit means 17 can be evaluated in various different ways to determine if these conditions are suitable for detecting abnormal infusion. This can be accomplished, for example, by comparing a function of the pressure of the fluid in the conduit means 17 during the normal delivery pattern 25 to a threshold. Although the function of the pressure of the fluid in the conduit means 17 can be the raw pressure samples from the A/D converter 57 per se, preferably this function includes some form of smoothing. According to a preferred technique, the following equation is used:

$$BQI = B1 + K(B2)$$

where, BQI is a baseline quality index, B1 is the magnitude of the baseline 77 prior to the valley 27, K is a constant which may be, for example, 3 and B2 is the rms value of a plurality, such as 120, of baseline 77 magnitudes occurring just prior to the baseline magnitude representing B1. Thus, BQI is a function of the pressure in the conduit means 17. Assuming that the pressure response 65 is slew-rate limited, averaged and low-pass filtered to determine the baseline 77 as described above, then B1 is the last baseline 77 value prior to the valley 27, and B2 is the rms value of 120 baseline values immediately preceding the value used for determining B1.

It has been found that, if BQI as calculated using the equation set forth above exceeds a threshold, the pressure conditions in the conduit means 17 are not suitble for determining whether or not abnormal infusion exists. Although this threshold can be adjusted as desired, by way of example, a threshold of 85 mmHg is suitable for many applications.

Figure 5A:
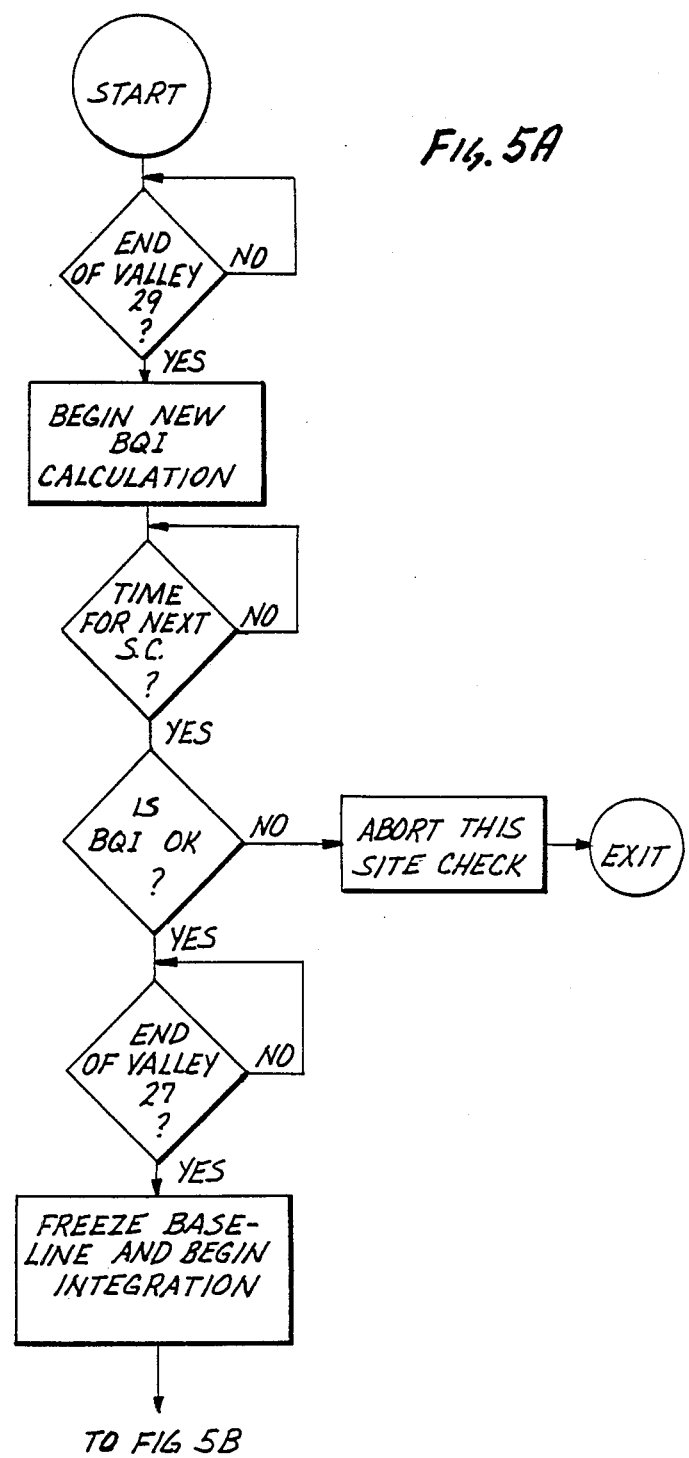
FIGS. 5a and 5b are a flow chart showing how the system functions to detect infiltration.
Figure 5B:
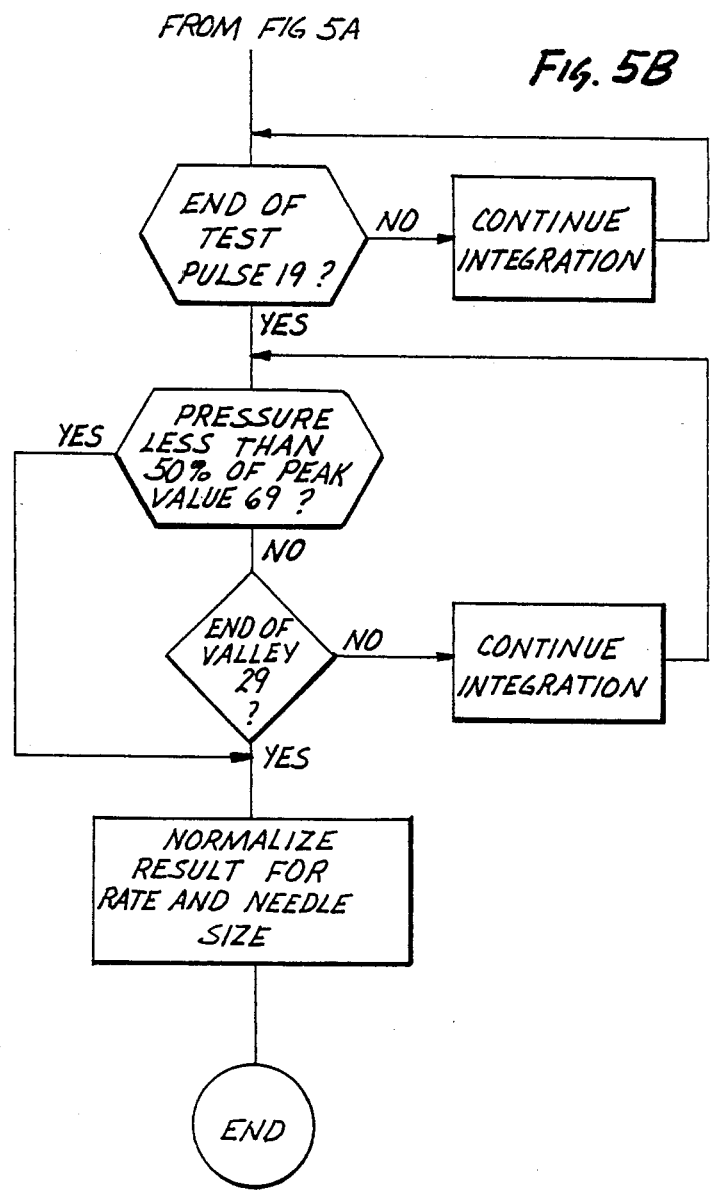

FIGS. 5a and 5b is a flow chart showing the basic steps in the truncated integration process of this invention. As shown in FIG. 5a, when the end of the valley 29 occurs, a new BQI calculation commences using the BQI equation set forth above. When the time for the next site check, i.e., the time to initiate the altered infusion pattern represented by the valley 27, the test pulse 19, and the valley 29 occurs, it is allowed to proceed only if the BQI is below the threshold magnitude as described above. In this regard, the next site check referred to in FIG. 5a may be manually initiated by entering information into the infusion device 15 or in response to programming of the infusion device 15 to provide site checks at specified times or at specified intervals. In any event, the infusion device 15, and in particular, the infusion pump 20 will provide the reduced infusion represented by the valley 27 only if the BQI is below the specified threshold.

When the end of the valley 27 is detected, i.e., the start of the test pulse 19, the baseline 77 is frozen and integration of the difference between the baseline and the pressure wave response commences as shown in FIG. 5a. The integration continues from the initial point 73 beyond the end of the test pulse 19 until the first to occur of a pressure less than 50 percent of the peak value 69 or the end of the trailing valley 29 as shown in FIG. 5b. At the end of the integration, the truncated area and the front end areas are normalized for infusion rate and needle-size effects as described above. Following this, the microprocessor 59 makes a decision concerning abnormal infusion as described above, and if infusion is abnormal, the alarm 63 is energized and/or infusion is terminated. Of course, the microprocessor may require information from multiple site checks before declaring abnormal infusion.

The abnormal infusion may be the result of any condition, such as infiltration, occlusion of the conduit means 17, clotting or phlebitis, which leads to the creation of the pressure wave response 67 (FIG. 4). In any event, once the abnormal infusion is declared, an attendant can determine the particular cause and seek to remedy it.

Although an exemplary embodiment of the invention has been shown and described, many changes, modifications and substitutions may be made by one having ordinary skill in the art without necessarily departing from the spirit and scope of this invention.

We claim:

1. An infusion system for infusing a fluid into a patient comprising:
   an infusion device for delivering the fluid, said infusion device including means for delivering the fluid in a normal delivery pattern and for delivering a test pulse of the fluid with the test pulse being distinguishable from the normal delivery pattern;
   conduit means for conducting the fluid from the infusion device to the patient, said test pulse creating a pressure wave response in the conduit means;
   means for determining the area between a baseline and at least a portion of a pressure versus time curve representing the pressure wave response; and
   means responsive to the magnitude of said area for detecting if the fluid is being improperly supplied by the conduit means to the patient.

2. An infusion system as defined in claim 1 wherein the pressure wave response has a peak value of pressure and a leading portion and a trailing portion on opposite sides of the peak value and said determining means determines the area from an initial point on the leading portion side of the peak value to a truncation point with the truncation point being on a portion of said curve corresponding to the trailing portion of the pressure wave response.

3. An infusion system as defined in claim 2 wherein said determining means establishes the truncation point as a percent of the peak value.

4. An infusion system as defined in claim 1 including means for establishing the baseline as essentially constant for the determination of said area.

5. An infusion system as defined in claim 1 including means for determining the baseline for use in the determination of said area as a function of the pressure in the conduit means when the test pulse is not present.

6. An infusion system as defined in claim 1 including first means responsive to the pressure of the fluid in the conduit means during the normal delivery pattern to ascertain if pressure conditions in the conduit means are suitable for detecting if fluid is being improperly supplied by the conduit means to the patient.

7. An infusion system as defined in claim 1 including ascertaining if pressure conditions in the conduit means are suitable for detecting if fluid is being improperly supplied by the conduit means to the patient.

8. A method for determining if a fluid is being properly supplied to a patient by an infusion system, said method comprising:
   delivering the fluid through conduit means to a patient's vascular system in a normal delivery pattern and in a test pulse, with the test pulse being distinguishable from the normal delivery pattern and with the test pulse creating a pressure wave response in the conduit means;
   determining the area between a baseline and at least a portion of a pressure versus time curve representing the pressure wave response; and
   using the magnitude of said area to detect if the fluid is being improperly supplied by the conduit means to the patient.

9. A method as defined in claim 8 wherein the pressure wave response has a peak value of pressure and a leading portion and a trailing portion on opposite sides of the peak value and said step of determining includes determining the area from an initial point on the leading portion side of the peak value to a truncation point with the truncation point being on a portion of said curve corresponding to the trailing portion of the pressure wave response.

10. A method as defined in claim 9 wherein said step of determining includes determining the truncation point as a percent of the peak value.

11. A method as defined in claim 8 including holding the baseline as essentially constant for the determination of said area.

12. A method as defined in claim 8 including establishing the baseline for use in the determination of said area as a function of the pressure in the conduit means when the test pulse is not present.

13. An apparatus for determining if fluid is being properly supplied through a fluid delivery system to a patient, said apparatus comprising:
 means for delivering fluid through the delivery system so as to create a pressure wave response in the delivery system;
 means for determing the area between a baseline and at least a portion of a pressure versus time curve representing the pressure wave response; and
 means responsive to the magnitude of said area for detecting if the fluid is being improperly supplied by the fluid delivery system to the patient.

14. An apparatus as defined in claim 13 wherein the pressure wave response has a peak value of pressure and a leading portion and a trailing portion on opposite sides of the peak value and said determining means determines the area from an initial point on the leading portion side of the peak value to a truncation point with the truncation point being on a portion of said curve corresponding to the trailing portion of the pressure wave response.

15. An apparatus as defined in claim 14 wherein said truncation point is essentially outside the noise range.

16. An apparatus as defined in claim 14 wherein said truncation point is at a time at which the pressure is no less than about 30 percent of the peak value.

17. An apparatus as defined in claim 14 wherein said truncation point is at a time at which the pressure is no greater than about 70 percent of the peak value.

18. An apparatus as defined in claim 14 wherein said truncation point is at a time at which the pressure is between about 30 percent to about 70 percent of the peak value.

19. An apparatus as defined in claim 14 wherein said truncation point is at a time at which the pressure is about 50 percent of the peak value.

20. An apparatus as defined in claim 14 wherein the initial point is essentially at the beginning of the point on said curve corresponding to the beginning of the pressure wave response.

21. An apparatus as defined in claim 14 including first means responsive to the pressure in the delivery system when the pressure wave response is not present to ascertain if pressure conditions in the delivery system are suitable for detecting if fluid is being improperly supplied by the delivery system to the patient.

22. An apparatus as defined in claim 21 wherein said first means includes means for comparing a function of the pressure of the fluid in the conduit means during the normal delivery pattern to a threshold to ascertain if pressure conditions in the conduit means are suitable for detecting if fluid is being improperly supplied by the conduit means to the patient.

23. An apparatus as defined in claim 13 including means for establishing the baseline as essentially constant for the determination of said area.

24. An apparatus as defined in claim 13 including means for determining the baseline for use in the determination of said area as a function of the pressure in the delivery system when the pressure wave response is not present.

25. An apparatus as defined in claim 24 wherein the truncation point is at a time at which the pressure is between about 30 percent to about 70 percent of the peak value, the initial point is essentially at the beginning of the point on said curve corresponding to the beginning of the pressure wave response and said baseline determining means establishes the baseline as essentially constant for the determination of said area.

26. An apparatus as defined in claim 13 including means for establishing the baseline including means for averaging the pressure in the delivery system during at least a portion of the time that the pressure wave response is not present.

27. An apparatus as defined in claim 13 including means for establishing the baseline including means for sampling the pressure in the delivery system during at least a portion of the time that the pressure wave response is not present to provide a plurality of samples, means for averaging said samples and means for excluding from said average at least the portion of any of said samples which exceeds a threshold.

28. An apparatus as defined in claim 13 wherein said detecting means includes means for normalizing said area and comparing the normalized area to a threshold.

29. An apparatus as defined in claim 13 wherein the pressure wave response has a peak value of pressure and a leading portion and a trailing portion on opposite sides of the peak value and said determining means determines the area from an initial point on the leading portion side of the peak value to about the peak value of pressure.

30. An apparatus as defined in claim 29 wherein the area between the initial point and about the peak value is a front end area and the determining means also determines the truncated area between the initial point and a truncation point with the truncation point being on a portion of said curve corresponding to the trailing portion of the pressure wave response and said detecting means is responsive to said front end area and said truncated area to detect if the fluid is being improperly supplied by the conduit means to the patient.

31. An infusion system for infusing a fluid into a patient comprising:
 an infusion device for delivering the fluid, said infusion device including means for delivering the fluid in a normal delivery pattern and for delivering the fluid in an altered pattern, said altered pattern including a test pulse and leading and trailing separating regions on opposite sides of the test pulse each of which provides a different flow rate of fluid than the adjacent portions of the test pulse;
 conduit means for conducting the fluid from the infusion device to the patient, said test pulse creating a pressure wave response in the conduit means;
 means for establishing a baseline as a function of the pressure in the conduit means when the test pulse is not present;
 means for determining the area between said baseline and a pressure versus time curve representing the pressure wave response between about the start of the pressure wave response and a truncation point which occurs after a peak value of the pressure wave response and before the end of the pressure wave response; and
 means responsive to the magnitude of said area for detecting if the fluid is being improperly supplied by the conduit means to the patient.

32. An infusion system as defined in claim 31 wherein said determining means establishes the truncation point as a percent of the peak value.

33. An infusion system as defined in claim 32 wherein said determining means establishes the truncation point as the first to occur of said percent of peak value and the end of said trailing valley.

34. An infusion system as defined in claim 33 wherein the baseline establishing means establishes said baseline as substantially constant for the measurement of said area.

35. An infusion system as defined in claim 31 wherein the test pulse provides a greater flow rate of fluid than the normal delivery pattern and the separating regions are valleys each of which provides a lesser flow rate of fluid than said adjacent portions of the test pulse.

36. An infusion system as defined in claim 35 wherein the detecting means includes means for dividing said area by a divisor which is a function of the difference between the flow rate during at least one of the valleys and the test pulse to provide a quotient and means for comparing the quotient to a threshold.

37. An infusion system as defined in claim 31 including first means responsive to the pressure of the fluid in the conduit means during the normal delivery pattern to ascertain if pressure conditions in the conduit means are suitable for detecting if fluid is being improperly supplied by the conduit means to the patient.

38. An infusion system as defined in claim 37 wherein said first means includes means for comparing a function of the pressure of the fluid in the conduit means during the normal delivery pattern to a threshold to ascertain if pressure conditions in the conduit means are suitable for detecting if fluid is being improperly supplied by the conduit means to the patient.

39. An infusion system as defined in claim 38 wherein said function of the pressure equals $B1+K(B2)$ where B1 is the baseline pressure at an instant prior to the test pulse, K is a constant and B2 is the rms value of a plurality of segments of the baseline pressure prior to the test pulse and with at least one of said segments being prior to said instant.

40. An infusion system for infusing a fluid into a patient comprising:
an infusion device for delivering the fluid, said infusion device including means for delivering the fluid in a normal delivery pattern and for delivering a test pulse of the fluid with the test pulse being distinguishable from the normal delivery pattern;
conduit means for conducting the fluid from the infusion device to the patient, said test pulse creating a pressure wave response in the conduit means;
first means responsive to the pressure of the fluid in the conduit means during the normal delivery pattern to ascertain if pressure conditions in the conduit means are suitable for detecting if fluid is being improperly supplied by the conduit means to the patient; and
means responsive to the pressure wave response for detecting if fluid is being improperly supplied by the conduit means to the patient.

41. An infusion system as defined in claim 40 wherein said first means includes means for comparing a function of the pressure of the fluid in the conduit means during the normal delivery pattern to a threshold to ascertain if pressure conditions in the conduit means are suitable for detecting if fluid is being improperly supplied by the conduit means to the patient.

42. An infusion system as defined in claim 41 wherein said function of the pressure equals $B1+K(B2)$ where B1 is the baseline pressure at an instant prior to the test pulse, K is a constant and B2 is the rms value of a plurality of segments of the baseline pressure prior to the test pulse and with at least one of said segments being prior to said instant.

43. An apparatus for determining if fluid is being properly supplied through a fluid delivery system to a patient, said apparatus comprising:
means for delivering fluid through the delivery system so as to create a pressure wave response in the delivery system;
first means responsive to the pressure in the delivery system when the pressure wave response is not present to ascertain if pressure conditions in the delivery system are suitable for detecting if fluid is being improperly supplied by the delivery system to the patient; and
means responsive to the pressure wave response for detecting if fluid is being improperly supplied by the delivery system to the patient.

44. An apparatus as defined in claim 43 wherein said first means includes means for comparing a function of the pressure of the fluid in the delivery system during the normal delivery pattern to a threshold to ascertain if pressure conditions in the delivery system are suitable for detecting if fluid is being improperly supplied by the delivery system to the patient.

45. An apparatus as defined in claim 44 wherein said function of the pressure equals $B1+K(B2)$ where B1 is the baseline pressure at an instant prior to the test pulse, K is a constant and B2 is the rms value of a plurality of segments of the baseline pressure prior to the test pulse and with at least one of said segments being prior to said instant.

* * * * *